United States Patent [19]
Heise et al.

[11] Patent Number: 5,498,749
[45] Date of Patent: Mar. 12, 1996

[54] PROCESS FOR SEPARATING CYCLOHEXANE DIMETHANOL FROM DIMETHYL TEREPHTHALATE

[75] Inventors: William H. Heise; Daniel P. Folk; Cheuk C. Yau; Chester W. Sink, all of Kingsport, Tenn.

[73] Assignee: Eastman Chemical Company, Kingsport, Tenn.

[21] Appl. No.: 139,672

[22] Filed: Oct. 22, 1993

[51] Int. Cl.$^6$ .................................................. C07C 67/54
[52] U.S. Cl. ............................................................ 560/78
[58] Field of Search .................................................. 560/78

[56] References Cited

U.S. PATENT DOCUMENTS

| | | | |
|---|---|---|---|
| Re. 32,241 | 9/1986 | Saxer | 62/542 |
| 2,828,330 | 3/1958 | Sinn | 260/475 |
| 3,037,050 | 5/1962 | Heisenberg et al. | 260/475 |
| 3,321,510 | 5/1967 | Lotz et al. | 260/475 |
| 3,488,298 | 1/1970 | Barkey et al. | 260/2.3 |
| 3,502,711 | 3/1970 | Claybaugh et al. | 260/475 |
| 3,701,741 | 10/1972 | Meyer et al. | 260/2.3 |
| 3,776,945 | 12/1973 | Ligorat | 260/475 D |
| 4,163,860 | 8/1979 | Delattre et al. | 560/96 |
| 4,578,502 | 3/1986 | Cudmore | 560/79 |
| 4,683,034 | 7/1987 | Bader | 203/43 |
| 5,051,528 | 9/1991 | Naujokas | 560/78 |

FOREIGN PATENT DOCUMENTS

| | | |
|---|---|---|
| 0484963 | 5/1992 | European Pat. Off. . |
| 1247291 | 8/1967 | Germany . |

Primary Examiner—Jos" G. Dees
Assistant Examiner—Rosalynd A. Williams
Attorney, Agent, or Firm—Bernard J. Graves, Jr.; Harry J. Gwinnell

[57] ABSTRACT

Provided is a method useful for separating and removing impurities such as cyclohexane dimethanol (CHDM) and other additives from their mixture with dimethylterehthalate (DMT), formed during a depolymerization process such as methanolysis of poly(ethyene terephthalate) (PET), poly(cyclohexyldimethylene terephthalate) (PCT), or copolyers of PET and PCT. The separation and removal of CHDM is accomplished via either melt or solution crystallization of the DMT following excess methanol removal (via distillation) of the methanolysis reactor products.

15 Claims, 3 Drawing Sheets

Schematic for Melt Crystallization of DMT

Fig. 1 Schematic for Melt Crystallization of DMT

Schematic for
Methanol Solution Crystallization of DMT

Schematic for
EG Solution Crystallization of DMT

PROCESS FOR SEPARATING CYCLOHEXANE DIMETHANOL FROM DIMETHYL TEREPHTHALATE

FIELD OF THE INVENTION

This invention relates to polyester chemistry. In particular, it relates to a process for separating polymer additives such as cyclohexane dimethanol from dimethyl terephthalate, in for example, a purification stream from the methanolysis of a polyester such as poly(ethylene terephthalate) or poly(cyclohexyldimethylene terephthalate).

BACKGROUND OF THE INVENTION

U.S. Pat. No. 3,776,945 teaches a process of depolymerizing poly(ethylene terephthalate) waste to obtain dimethyl terephthalate and ethylene glycol by subdividing the waste into dimensions between 4 and 35 mesh and treating at a temperature of 100° C. to 300° C. and a pressure from 1 to 150 atmospheres with methanol in a quantity that the proportion of methanol to waste is between 1:1 and 10:1 by weight in the presence of acid catalysts.

U.S. Pat. No. 3,321,510 relates to a process of decomposing poly(ethylene terephthalate) by first treating with steam at a temperature of from about 200° C. to 450° C. and then reducing the steam-treated poly(ethylene terephthalate) in the form of a brittle solid product to a powder having a mean particle size of from about 0.0005 to 0.002 millimeters and subsequently atomizing the fine powder with a gaseous substance including inert gas and methanol vapor to form an aerosol which is conducted through a reaction zone at a temperature of 250° C. to 300° C. in the presence of excess methanol vapors.

U.S. Pat. No. 3,037,050 relates to the recovery of terephthalic acid dimethyl ester by treating poly(ethylene terephthalate) in the form of bulky or lumpy solid masses with super-heated methanol vapor in the presence of any suitable esterification catalyst substantially at atmospheric pressure.

U.S. Pat. No. 4,578,502 relates to a procedure for recovering monomeric polycarboxylic acids and polyols from solid scrap polyesters by granulating the scrap resin, slurrying the resin with sufficient solvents such as water or methanol, depolymerizing the slurried resin by the application of heat and pressure for a time sufficient to convert substantially all of the resin into its monomeric components, crystallizing the monomeric polycarboxylic acid present by flash crystallization and recovering the polycarboxylic acid and then the polyol by distillation.

U.S. Pat. No. 4,163,860 relates to a process for converting a bis-(diol) terephthalate to dimethyl terephthalate by interchange in a substantially anhydrous methanol medium in the presence of a magnesium methylate catalyst.

U.S. Pat. No. 3,701,741 relates to a method of recovering substantially pure poly(ethylene terephthalate) from scrap poly(ethylene terephthalate) contaminated with impurities by dissolving the contaminated material at elevated temperatures and super-atmospheric pressure in a volatile solvent. This patent does not relate to the recovery of the monomeric ingredients that comprise the polymer.

U.S. Pat. No. 3,488,298 relates to a process for recovering dimethyl terephthalate and ethylene glycol from poly(ethylene terephthalate) scrap by forming a mixture comprising the poly(ethylene terephthalate) scrap, catalyst and methanol, heating the mixture to approach equilibrium, treating the partially hydrolyzed mixture with an excess of phosphorus-containing compound, heating the treated mixture to fractionate the constituents and recovering methanol, ethylene glycol and dimethyl terephthalate.

U.S. Pat. No. 5,051,528 claims a process for recovering ethylene glycol and dimethyl terephthalate from poly(ethylene terephthalate) polyesters which comprises dissolving scrap polyester in oligomers of ethylene glycol and terephthalic acid or dimethyl terephthalate, passing superheated methanol through the solution and recovering the ethylene glycol and dimethylterephthalate.

Scrap, off-class production, and consumer waste poly(ethylene terephthalate) (PET) and its copolymers may be depolymerized using methanol to its monomeric components for reuse in PET production. However, there is a need to provide consistently high-purity raw materials for PET production to maintain polymer properties such as color, melting point, impact strength, and melt viscosity. Typically the PET waste stream contains polymer produced from different resin producers who use various polymer modifiers to impart specific PET properties. During the methanolysis depolymerization process, these modifiers are present as impurities which need to be removed from the main reaction products of dimethyl terephthalate (DMT) and ethylene glycol (EG). Examples of these impurities include cyclohexane dimethanol (CHDM), dimethyl isophthalate (DMI), diethylene glycol (DEG), and triethylene glycol (TEG).

European Patent Application Publication No. 484963 A2 describes a process for the preparation of dimethyl terephthalate from polymers of terephthalic acid and a glycol which comprises treating said polymers in a reaction zone with methanol vapors at a temperature above 230° C. and at a pressure below about 15 atmospheres, continuously removing vapors of methanol, dimethyl terephthalate, and the glycol from the reaction zone, said vapors containing at least about 3 moles of methanol for every mole of dimethyl terephthalate, separating methanol from said vapors, and separating dimethyl terephthalate from the vapors.

The present invention as described below provides a process yielding high purity DMT which can be used for further polymer production. Simple product separation by conventional distillation is not feasible due to the relatively close boiling points of several of these impurities to DMT. Further, the existence of low-boiling azeotropes of the glycols with DMT result in unacceptable DMT yield losses when employing distillation alone.

Previous patents dealing with the depolymerization of PET have addressed the reaction mechanisms for the depolymerization reaction. Purification of DMT as related to its separation from EG is addressed in U.S. Pat. No. 4,578,502, yet no mention is made of removal of CHDM, DMI, or other glycols. Distillation is unsuitable for the removal of CHDM, DEG, and TEG due to the presence of close boiling points and minimum boiling azeotropes. The separation of DMT by melt crystallization from products from oxidation of p-xylene and subsequent esterification with methanol is taught by U.S. Pat. No. 4,683,034. However, in this system, no CHDM impurities are present which, at levels well below 0.5 wt %, will cause off-specification PET production.

SUMMARY OF THE INVENTION

The invention relates to a process for separating and removing impurities such as cyclohexane dimethanol (CHDM) and other additives from their mixture with dimethyl terephthalate (DMT), formed during a depolymerization process such as methanolysis of poly(ethylene terephthalate) (PET), poly(cyclohexyldimethylene terephthalate) (PCT), or copolymers of PET and PCT. The separation and removal of CHDM is accomplished via crystallization of the DMT following excess methanol removal (via distillation) of the methanolysis reactor products.

DETAILED DESCRIPTION OF THE INVENTION

This invention provides a process yielding high purity DMT via a crystallization process to remove polyester methanolysis reaction by-products, such as CHDM and DMI. The invention comprises the use of either melt crystallization or solution crystallization from ethylene glycol, methanol, or a combination of the two. The solution crystallization alternatives may involve one or more crystallization steps.

Scheme 1: Melt Crystallization

Figure 1:
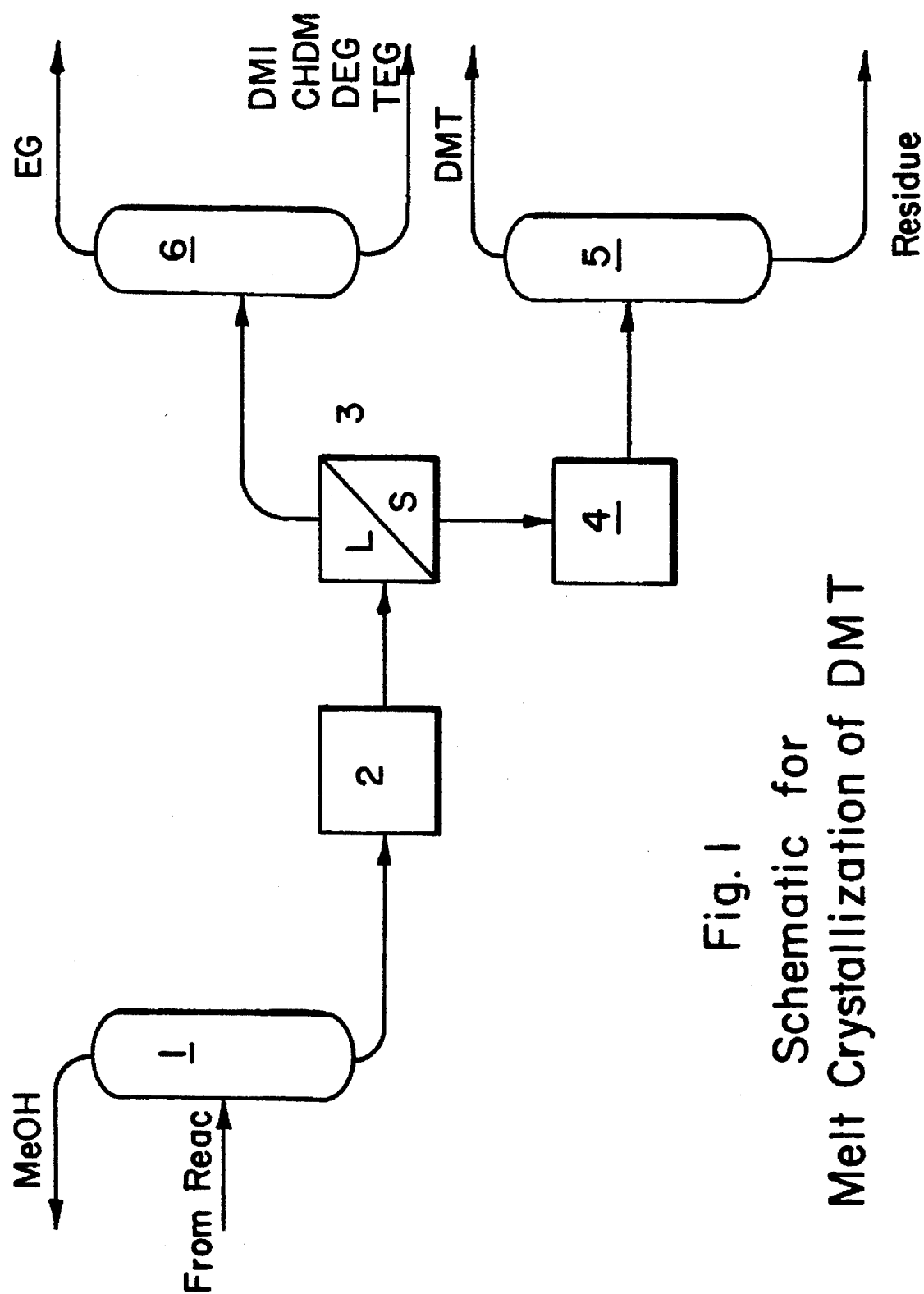
FIG. 1 is a schematic of a preferred method for purifying DMT utilizing melt crystallization.

FIG. 1 is a schematic of the purification of DMT via melt crystallization. The process involves removing the methanol in a distillation or stripping column (1), while underflowing a mixture of ethylene glycol, DMT and other impurities. This mixture may then be fed to a melt crystallization system (2), or, alternatively, a distillation column may be used to first remove the EG prior to feeding a suspension growth melt crystallizer such as a scraped surface vessel type crystallizer. The stream is then allowed to separate in a solid/liquid separation unit (3), and the liquid portion distilled in an ethylene glycol refining column (6). The solids from (3) are melted in a melter (4) and optionally subjected to distillation (5) to provide highly pure dimethylterephthalate and a residue. Alternatively, the functions of (2), (3), and (4), can be performed in a single layer growth melt crystallizer vessel (e.g., as described by Saxer, U.S. Pat. No. Reissue 32,241, incorporated herein by reference). Other melt crystallizers such as static plate and tube crystallizers may be utilized. (See, for example, U.S. Pat. No. 4,683,034, incorporated herein by reference.)

An example of successive product purification via batch melt crystallization studies is shown in the following table. These data were collected by successive partial freezing, draining the liquid fraction, and removing the product fraction by melting. The number of melt crystallization cycles required is dependent on the initial feed composition and the desired impurity concentration in the product. Other species typical of a methanolysis stream were added to the initial feed streams (such as EG, DMI, and DEG), and their relative fractions are not reported in this table.

TABLE 1

Removal of CHDM from DMT by Melt Crystallization

| Cycle No. | Feed Composition | | Product Composition | | Product Melt Temp (C.) |
|---|---|---|---|---|---|
| | % DMT | % CHDM | % DMT | % CHDM | |
| 1 | 63.2 | 8.6 | 74.7 | 5.9 | 128.3 |
| 2 | 72.2 | 6.7 | 91.2 | 2.3 | 135 |
| 3 | 84.1 | 3.2 | 93.1 | 1.4 | 137.1 |
| 4 | 93.1 | 1.4 | 97.9 | 0.5 | 139.5 |
| 5 | 97.9 | 0.5 | >99 | 816 ppm | 140.5 |
| 6 | >99 | 816 ppm | >99.9 | 21 ppm | 140.6 |

Relatively short residence times in the melt crystallization unit and associated feed, interstage, and product tanks are preferred in order to prevent thermally catalyzed repolymerization of the DMT with the glycols present in the system.

Thus, the present invention provides a method for purifying dimethyl terephthalate in a product stream from the methanolysis of polyesters comprised of residues of terephthalic acid, which comprises the steps:

(a) subjecting said product stream to distillation, thereby removing excess methanol;

(b) crystallizing crude dimethyl terephthalate to form a solid/liquid mixture;

(c) separating said solid from the solid/liquid mixture, remelting said solid to form a melt; and optionally (d) subjecting said melt to distillation and isolating dimethyl terephthalate as a vapor.

Scheme 2: Solution Crystallization from Methanol

Figure 2:
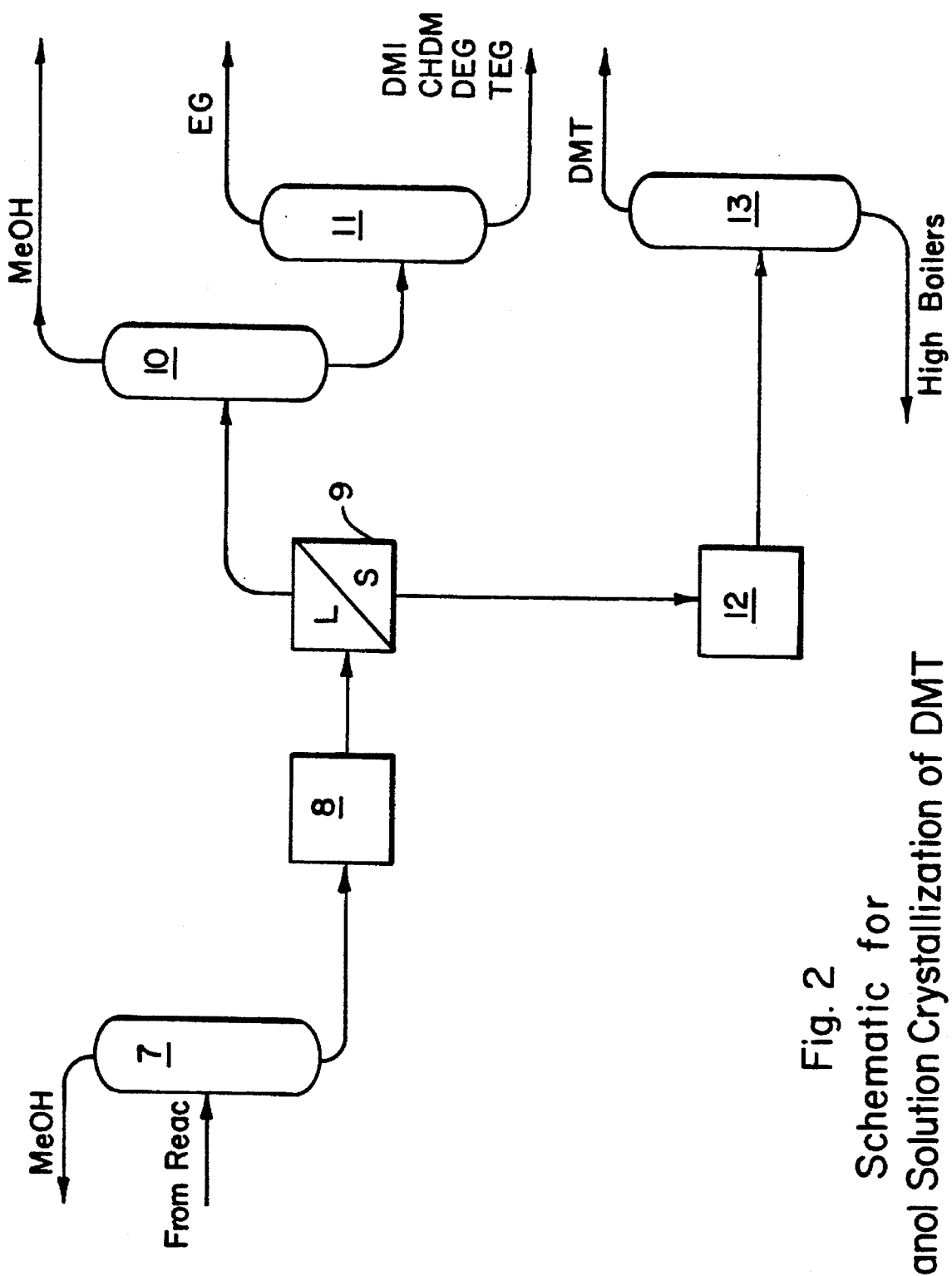
FIG. 2 is a schematic of a preferred method for purifying DMT utilizing solution (methanol) crystallization.

The process schematic in which DMT purification can be performed via solution crystallization from methanol is shown in FIG. 2. This scheme involves removing excess methanol from the reaction products in a stripping column (7) to produce a stream containing between about 20 and 30 wt % DMT as feed to the crystallization unit(s) (8). It is preferred that this crystallization is conducted over a range of about 125° C. to about 5° C., with about 105° C. to about 25° C. being especially preferred for a 30% solution (by weight). A solution temperature above the DMT saturation temperature allows transfer between vessels without plugging lines or encrusting portions of the vessel from the uncontrolled crystallization of DMT on slightly cooler surfaces. The preferred starting temperature for the 30% DMT solution is 5° C. above its saturation temperature. Temperatures below 100° C. cannot be used to maintain the 30% DMT in solution. The preferred starting temperature for a 20% DMT solution is 95° C. using the above criteria. A crystallization starting temperature of 108° C. was used in the laboratory, cooling to a final crystallization temperature of 25° C. The rate of cooling ranges from 10° to 25° C./hr and is not critical in achieving the purification by crystallization within this range. In the crystallization step, it is required that the minimum pressure correspond in the range of about 32 psi for the 30% DMT solution. In our experiments, initial crystallization pressures ranged from 52 to 75 psig. Cooling may be accomplished through conductive heat transfer through heat exchange surface or may be removed as the latent heat through evaporation and the condensation of the methanol solvent. In the latter, the temperature is preferably reduced as the pressure is lowered (e.g., 2 psia to reach 25° C.) In general, the pressure is at or above the vapor pressure of the liquid at the temperature of the liquid.

The product from (8) is then transferred to a solid/liquid separation unit (9), which provides a crude cake containing approximately 85 wt % DMT, 12 wt % methanol, 0.1 wt % CHDM, and the remainder EG and DEG. Following a methanol wash at a range of about 0°–50° C., preferably at about 15° C.–25° C., most preferably at about 20° C., the wet cake product contained 26 ppm CHDM using a weight ratio of 1.5 to 2 times as much methanol to crude cake. The amount of methanol used in the washing step affects the DMT product yield since DMT is slightly soluble in methanol. (See Table 2.)

The liquid portion from (9) is then subjected to distillation in a methanol refining column (10) and methanol removed. The lower stream from (10) is subjected to distillation in an ethylene glycol refining column (11). The methanol-wet solid portion from (9) is melted in a melter (12) from which the methanol can be removed by evaporation. Optionally, this material can be subjected to distillation in a dimethyl terephthalate column (13).

TABLE 2

Effect of the Amount of Wash Methanol on DMT Product Recovery

| Wash Amount Lb Methanol/Lb Dry DMT | DMT Product Recovery, % |
|---|---|
| 2.3 | 95.4 |
| 1.15 | 96.8 |
| 0 | 97.7 |

As shown in FIG. 2, to remove residual methanol, the DMT is melted.

Thus, as a further aspect of the present invention, there is provided a method for purifying dimethyl terephthalate in a product stream from the methanolysis of polyesters comprised of residues of terephthalic acid, which comprises the steps:

(a) subjecting said product stream to distillation, thereby removing excess methanol;

(b) crystallizing crude dimethyl terephthalate in methanol in a concentration of about 10 to about 40% by weight to form a solid/liquid mixture;

(c) separating said solid from the solid/liquid mixture, remelting said solid to form a melt; and optionally (d) subjecting said melt to distillation and isolating dimethylterephthalate as a vapor.

Scheme 3: Solution Crystallization from Ethylene Glycol

Figure 3:
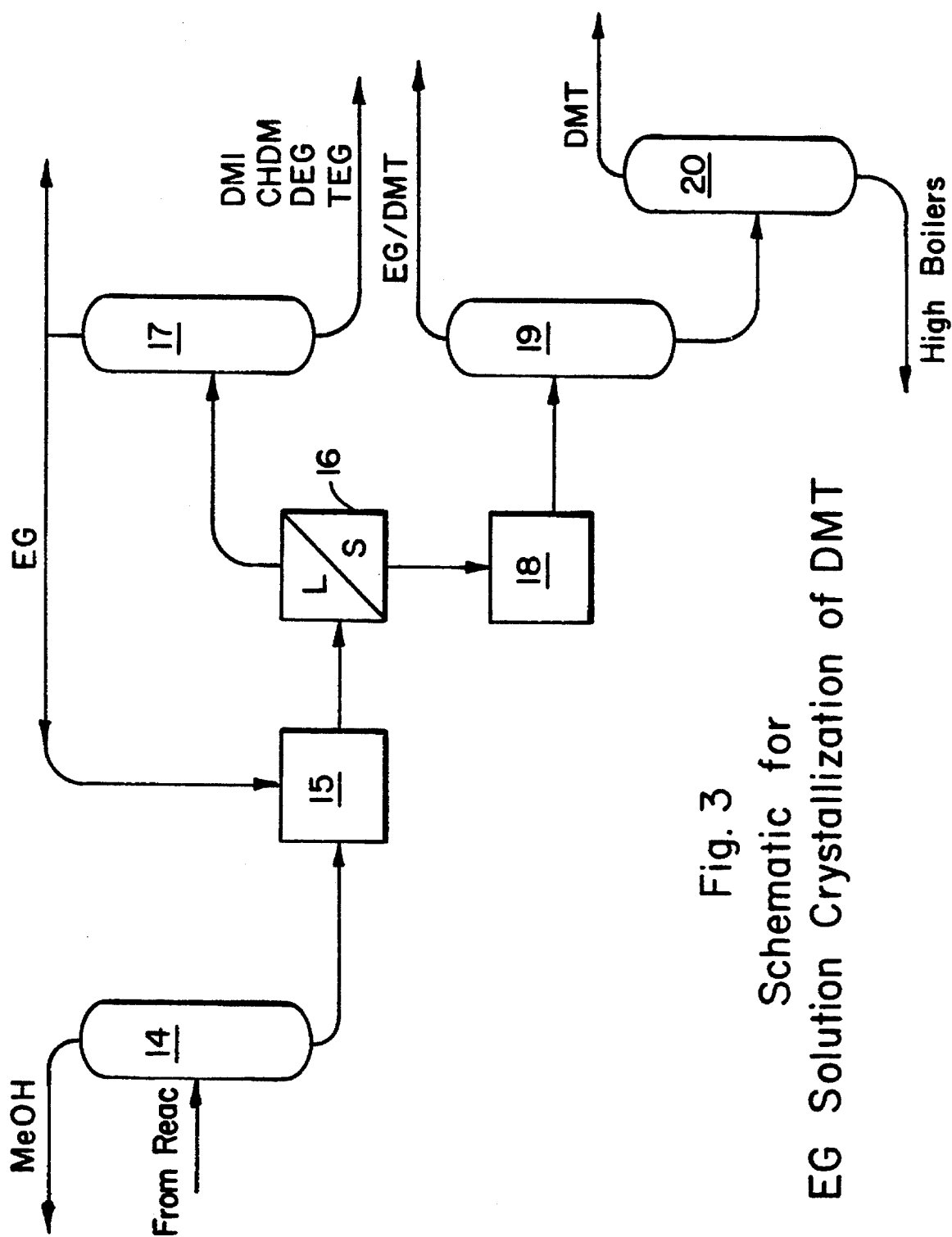
FIG. 3 is a schematic of a preferred method for purifying DMT utilizing solution (ethylene glycol) crystallization.

FIG. 3 depicts a process schematic in which DMT is purified by means of solution crystallization from EG. In this scheme, all methanol is removed via a methanol stripping column (14), leaving a stream containing principally DMT, EG, DEG, DMI, and CHDM. Experimental feed conditions varied DMT concentration from 24 to 30 wt %. EG is then added in order to reach this DMT concentration range.

The initial crystallization temperatures in crystallizer (15) are preferably 110° C. to about 150° C., most preferably about 130° C. to about 135° C. In our experiments, initial crystallization temperatures ranging from 129° C. to 135° C. were employed, and final temperatures of 110° C. to 50° C. were examined from which a DMT product with less than 0.001% CHDM present was obtained. The final temperature range can be at least 110° C. to 50° C. At the highest final temperature, the separation of the impurity containing liquid from the DMT proceeds 4.5 times faster due to the lower viscosity of the solution (i.e., 14.3 gpm/ft2 v. 3.2 gpm/ft2 filtration flux). Also, evaporative cooling of the solution to this temperature is possible with simple vacuum systems generating 30 mm Hg (0.6 psia). Increasing the crystallizer product stream temperature will reduce the recovery of DMT in the solid product because of its increased solubility with temperature—approximately 70% at 110° C. from a 24% feed solution. Operating at the lower temperature allows a higher recovery (approx. 98% at 50° C.) of DMT, but cooling to 50° C. requires 1 mm Hg for evaporation, or scraped surface heat exchangers, or refrigerant sparged crystallizers, requiring more elaborate and expensive equipment. In general, the pressure is not critical, but a pressure ranging from atmospheric to about 1 mm Hg is preferred with a range of 15–45 mm Hg being most preferred.

The mother liquors from the solid/liquid separation unit (16) is subjected to distillation in an EG refining column (17) to remove impurities and the purified EG recycled for use in the crystallizer (15). The solid material from (16) is transferred to a melter (18) and subjected to distillation in an EG removal column (19). The underflow from column (19) is then optionally subjected to distillation in a distillation column (20) to provide highly purified DMT, although this step is not required to remove CHDM from DMT.

In the liquid/solid separation above (16), final cake conditions following washing with EG are reported in Table 3.

TABLE 3

Final Cake Compositions from EG Solution Crystallization

| Run | Final Cryst Temp. | % DMT | % EG | % DMI | % CHDM |
|---|---|---|---|---|---|
| 1 | 110° C. | 42.1 | 56.5 | <0.001 | <0.001 |
| 2 | 110° C. | 47.5 | 51.0 | <0.001 | <0.001 |
| 3 | 110° C. | 40.3 | 59.0 | <0.001 | <0.001 |
| 4 | 110° C. | 41.8 | 55.1 | <0.001 | <0.001 |
| 5 | 50° C. | 51.9 | 47.0 | 0.02 | <0.001 |
| 6 | 50° C. | 47.7 | 50.9 | 0.02 | 0.04 |
| 7 | 50° C. | 48.8 | 48.3 | 0.22 | 0.35 |

Runs 1 and 2 have an initial crystallization temperature of 129° C. to 130° C., respectively, while all the remaining runs began at 135° C.

No further experimental work was conducted with the wet cakes; however, the removal of DMI and CHDM were demonstrated. Drying or melting followed by distillation would be required to remove the ethylene glycol solvent. Alternatively, the DMT solids in ethylene glycol in the product filter cake could be melted and fed directly to a PET polymerization reactor. The correct stoichiometric ratios could be achieved with supplementary feeds.

Thus, as a further aspect of the present invention, there is provided a method for purifying dimethylterephthalate in a product stream from the methanolysis of polyesters comprised of residues of terephthalic acid, which comprises the steps:

(a) subjecting said product stream to distillation, thereby removing excess methanol;

(b) crystallizing crude dimethyl terephthalate in ethylene glycol in a concentration of about 10 to about 40 weight percent to form a solid/liquid mixture;

(c) separating said solid from the solid/liquid mixture, remelting said solid to form a melt;

(d) subjecting said melt to distillation to remove ethylene glycol; optionally followed by (e) subjecting the high boiling fraction from (d) to distillation and isolating dimethylterephthalate as a vapor.

Although both melt and solution crystallization are effective for removing glycols that will cause problems producing high quality PET, an advantage of the solution crystallization process is the operation at lower temperatures thereby minimizing the repolymerization of DMT.

We claim:

1. A method for purifying dimethyl terephthalate in a product stream from the methanolysis of polyesters comprised of residues of terephthalic acid, which comprises the steps:
    (a) subjecting said product stream to distillation, thereby removing excess methanol;
    (b) crystallizing crude dimethyl terephthalate to form a solid/liquid mixture;
    (c) separating said solid from the solid/liquid mixture, remelting said solid to form a melt; and optionally
    (d) subjecting said melt to distillation and isolating dimethyl terephthalate as a vapor.

2. The method of claim 1, further comprising the step of removing excess ethylene glycol prior to performing step (b).

3. The method of claim 1, wherein the temperature of crystallization step (b) is in a range of about 110° to about 140° C.

4. The method of claim 1, wherein the polyester is poly(ethylene terephthalate).

5. The method of claim 1, wherein the polyester is poly(cyclohexyldimethylene terephthalate).

6. The method of claim 1, wherein the polyester is copoly(ethylene cyclohexyldimethylene terephthalate).

7. A method for purifying dimethyl terephthalate in a product stream from the methanolysis of polyesters comprised of residues of terephthalic acid, which comprises the steps:
    (a) subjecting said product stream to distillation, thereby removing excess methanol;
    (b) crystallizing crude dimethyl terephthalate in methanol in a concentration of about 10 to about 40% by weight to form a solid/liquid mixture;
    (c) separating said solid from the solid/liquid mixture, remelting said solid to form a melt; and optionally
    (d) subjecting said melt to distillation and isolating dimethylterephthalate as a vapor.

8. The method of claim 7, wherein the crystallization step (b) is performed at a temperature of about 125° C. to about 5° C.

9. The method of claim 7, wherein the crystallization step (b) is performed at a temperature of about 105° C. to about 25° C.

10. The method of claim 7, wherein the concentration of crude dimethyl terephthalate is about 25–35% by weight.

11. A method for purifying dimethyl terephthalate in a product stream from the methanolysis of polyesters comprised of residues of terephthalic acid, which comprises the steps:
    (a) subjecting said product stream to distillation, thereby removing excess methanol;
    (b) crystallizing crude dimethyl terephthalate in ethylene glycol in a concentration of about 10 to about 40 weight percent to form a solid/liquid mixture;
    (c) separating said solid from the solid/liquid mixture, remelting said solid to form a melt;
    (d) subjecting said melt to distillation to remove ethylene glycol; optionally followed by
    (e) subjecting the high boiling fraction from (d) to distillation and isolating dimethylterephthalate as a vapor.

12. The method of claim 11, wherein the crystallization step (b) is performed at a temperature of about 115° C. to about 40° C.

13. The method of claim 11, wherein the crystallization step (b) is performed at a temperature of about 115° C. to about 100° C.

14. The method of claim 11, wherein the crystallization step (b) is conducted at a pressure of about atmospheric to about 1 mm Hg.

15. The method of claim 11, wherein the crystallization step (b) is conducted at a pressure of about 15 to 45 mm Hg.

* * * * *